(12) United States Patent
Dave et al.

(10) Patent No.: US 8,449,917 B2
(45) Date of Patent: May 28, 2013

(54) SOLID HERBICIDE COMPOSITIONS WITH BUILT-IN ADJUVANT

(75) Inventors: Hiteshkumar Dave, Carmel, IN (US); Lei Liu, Carmel, IN (US); Raymond E. Boucher, Jr., Lebanon, IN (US); David G. Ouse, Indianapolis, IN (US); Richard K. Mann, Franklin, IN (US); James M. Gifford, Lebanon, IN (US); Yi-hsiou Huang, Taiwan (CN); Åndrea C. McVeigh-Nelson, Indianapolis, IN (US); Martin C. Logan, Indianpolis, IN (US); Ashish Batra, Carmel, IN (US)

(73) Assignee: Dow AgroSciences, LLC, Indianapolis, IN (US)

( * ) Notice: Subject to any disclaimer, the term of this patent is extended or adjusted under 35 U.S.C. 154(b) by 0 days.

(21) Appl. No.: 13/182,470

(22) Filed: Jul. 14, 2011

(65) Prior Publication Data
US 2012/0015811 A1 Jan. 19, 2012

Related U.S. Application Data

(60) Provisional application No. 61/364,615, filed on Jul. 15, 2010.

(51) Int. Cl.
| | | |
|---|---|---|
| *A61K 9/14* | (2006.01) |
| *A61K 9/50* | (2006.01) |
| *A01N 43/40* | (2006.01) |
| *A01N 43/60* | (2006.01) |
| *A01N 43/54* | (2006.01) |
| *A01N 43/90* | (2006.01) |
| *A01N 43/76* | (2006.01) |
| *A01N 37/00* | (2006.01) |
| *A01N 37/34* | (2006.01) |

(52) U.S. Cl.
USPC .......... 424/489; 424/499; 424/500; 424/502; 504/130; 504/136; 504/239; 504/241; 504/242; 504/244; 504/251; 504/255; 504/260; 504/270; 504/307; 504/310

(58) Field of Classification Search
None
See application file for complete search history.

(56) References Cited

U.S. PATENT DOCUMENTS

| | | | |
|---|---|---|---|
| 5,137,726 A | 8/1992 | Ogawa et al. |
| 5,703,010 A | 12/1997 | Heinrich et al. |

FOREIGN PATENT DOCUMENTS

| | | | |
|---|---|---|---|
| CN | 101530106 | * | 4/2009 |
| JP | 9194302 A | | 7/1997 |
| WO | WO2009012979 A2 | | 1/2009 |
| WO | WO2009058717 A2 | | 5/2009 |

* cited by examiner

*Primary Examiner* — Alton Pryor
(74) *Attorney, Agent, or Firm* — Robert Chang

(57) ABSTRACT

The present invention concerns stable herbicidal solid compositions containing built-in adjuvant which exhibit improved herbicidal efficacy when used to control weeds in flooded rice paddies or fields.

49 Claims, No Drawings

SOLID HERBICIDE COMPOSITIONS WITH BUILT-IN ADJUVANT

CROSS REFERENCE TO RELATED APPLICATIONS

This application claims the benefit of U.S. Provisional Patent Application Ser. No. 61/364,615 filed Jul. 15, 2010.

FIELD OF THE INVENTION

This invention concerns stable solid compositions, such as granules and powders, containing herbicides and built-in adjuvant, and methods for their preparation and use. Such solid compositions exhibit improved herbicidal efficacy on weeds in flooded paddy rice applications.

BACKGROUND OF THE INVENTION

Agrochemical formulations are generally designed based on customer needs and the physiochemical properties of the active ingredients, for example, the solubility of the active ingredient in water or non-aqueous solvents. There are two major categories of formulations, solid formulations and liquid formulations.

Granule products containing agricultural active ingredients represent one class of solid formulations that are seeing increased use today because of their relative safety compared to liquid formulations and the advantages they offer with regard to cost savings in packaging and transportation. Granule products, in the form of emulsifiable granules (EG), water dispersible granules (DG) and granules (GR) for broadcast application, may be used for insect, weed, fungal pathogen and nematode control and are often used in soil and aquatic environments. Because of the particle weight, granules used in aerial applications may pose a reduced hazard from off-target drift compared to aerial liquid spray applications.

Powder or wettable powder (WP) products containing agricultural active ingredients represent additional classes of solid formulations that are also used in agriculture and differ from granules primarily by their smaller particle size. Granules typically have a size range between about 200 to about 4000 micrometers (Wikipedia: Granulation—making of granules) and are much larger than the particles in powder formulations and therefore present less of a respiratory hazard. Granule products may be produced from powders or wettable powders in a granulation or agglomeration process.

Active ingredients, in the form of solids or liquids, may be formulated as granules and include insecticides, herbicides, fungicides, nematicides and plant growth regulators. Granule formulations usually contain a relatively small amount of the active ingredient since the granules are frequently not further diluted with a carrier solvent such as water prior to use, but are instead applied directly to the area of interest, such as for example, soil or water. Once applied, the active ingredient contained in the granule is released to the area of application, typically upon exposure to water.

Agricultural granules containing active ingredients also contain solid inert ingredients that may serve as a diluent and/or help maintain the granules in a stable, solid state. These solid inert ingredients may include, for example, clays, starches, silicas, sulphates, chlorides, lignosulfonates, carbohydrates such as dextrines, alkylated celluloses, xanthum gums and guaseed gums, and synthetic polymers such as polyvinyl alcohols, sodium polyacrylates, polyethylene oxides, polyvinylpyrrolidones and urea/formaldehyde polymers like PergoPak M® (registered trademark of Albemarle Corporation). The active ingredient(s) contained in a granule may be melted into a liquid, dissolved in a solvent or dispersed in a liquid, which may then be sprayed onto or absorbed into the solid inert ingredients. In the absence of effective solid inert ingredients, dry granules may be physically unstable and, in the case of solid particles, slowly breakdown forming a dust or powder or, in the case of granules containing liquid built-in adjuvants, slowly breakdown forming large liquid droplets as a result of Ostwald Ripening. Many solid inert ingredients used in agricultural granule formulations generally have good water solubility or dispersibility.

Adjuvants are important components of granules and are defined as substances which can increase the biological activity of the active ingredient, but are themselves not significantly biologically active. Adjuvants assist with the effectiveness of the active ingredient such as, for example, by improving the delivery and uptake of an herbicide into a target weed plant leading to improved biological control.

Adjuvants, in the form of solids or liquids, can be added directly to a formulated agricultural product, such as a granule, to provide improved performance of the product upon application. Commonly used adjuvants may include, for example, surfactants, spreaders, petroleum and plant derived oils and solvents and wetting agents. Examples of commonly used adjuvants include, but are not limited to, paraffin oil, horticultural spray oils (e.g., summer oil), methylated rape seed oil, methylated soybean oil, highly refined vegetable oil and the like, polyol fatty acid esters, polyethoxylated esters, ethoxylated alcohols, alkyl polysaccharides and blends, amine ethoxylates, sorbitan fatty acid ester ethoxylates, polyethylene glycol esters, organosilicone based surfactants, ethylene vinyl acetate terpolymers, ethoxylated alkyl aryl phosphate esters and the like. These and other adjuvants are described in the "*Compendium of Herbicide Adjuvants, 9th Edition*," edited by Bryan Young, Dept. of Plant, Soil and Agricultural Systems, Southern Illinois University MC-4415, 1205 Lincoln Drive, Carbondale, Ill. 62901, which is available for viewing on the internet at http://www.herbicide-adjuvants.com/.

The term "built-in adjuvant" refers to one or more adjuvants that have been added to a particular formulation, such as a granule or liquid formulation, at the manufacturing stage of the product, rather than at the point of use of the product such as, for example, to a spray solution. The use of built-in adjuvants simplifies the use of agrochemical products for the end-user by reducing the number of ingredients that must be individually measured and applied.

Rice is an important cereal crop grown in many parts of the world and is cultivated under both wet and dry conditions. Control of weeds in rice is very important in order to maintain high levels of agricultural productivity. Use of herbicide granules for weed control in flooded rice paddies and fields is a very common agronomic practice in many rice growing regions. New herbicide granule products that offer improved performance relative to current products are needed.

Cyhalofop-butyl, (2R)-2-[4-(4-cyano-2-fluorophenoxy)phenoxy]propanoic acid butyl ester (CAS#122008-78-0), is a member of the aryloxyphenoxypropionic acid class of herbicides which are known in the art as the fop herbicides and is used to control grass weeds in rice. Cyhalofop-butyl is marketed as Clincher® herbicide (registered trademark of Dow AgroSciences LLC) and is sold in granule (GR), oil in water (EW) and emulsifiable concentrate (EC) formulations and exhibits good selectivity to rice when used in both dry land and flooded paddy applications.

Existing commercial granule formulations of cyhalofop-butyl contain relatively large amounts of solid inert ingredients such as potassium chloride, clay or starch combined with relatively small amounts of built-in adjuvants such as aromatic solvents. These built-in adjuvants consist of a maximum of from about 15 to about 20 per cent by weight relative to the total weight of the cyhalofop-butyl granule in currently marketed products. The limited built-in adjuvant content of current granule products can limit the biological performance of cyhalofop-butyl herbicide due to a minimal herbicidal adjuvant effect.

The present invention provides an improvement to existing solid herbicide compositions used to control weeds in rice by allowing higher loadings of built-in adjuvant and thereby offering improved herbicidal efficacy on weeds in flooded rice paddies or fields.

SUMMARY OF THE INVENTION

The present invention concerns a stable herbicide granule containing built-in adjuvant which comprises:
  a) an herbicide selected from the class of ACCase or ALS enzyme inhibitors comprising, with respect to the total composition, from about 1 gram per kilogram (g/kg) to about 200 g/kg;
  b) a built-in adjuvant comprising, with respect to the total composition, from about 50 g/kg to about 750 g/kg;
  c) a solid carbohydrate comprising, with respect to the total composition, from about 10 g/kg to about 700 g/kg; and
  d) a solid, water soluble polymer or oligomer comprising, with respect to the total composition, from about 50 g/kg to about 700 g/kg, with the proviso that the solid carbohydrate and the solid, water soluble polymer or oligomer must together comprise at least 200 g/kg of the total composition.

The present invention equally well concerns a stable herbicidal powder containing built-in adjuvant.

Another aspect of the present invention concerns a stable herbicidal solid composition containing built-in adjuvant which comprises:
  a) an herbicide selected from the compounds of the Formula

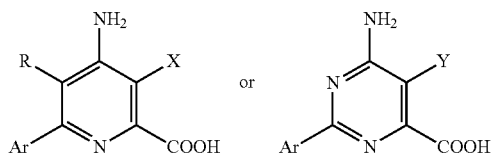

wherein
Ar represents a phenyl group substituted with one to four substituents independently selected from halogen, $C_1$-$C_6$ alkyl, $C_1$-$C_6$ alkoxy, $C_2$-$C_4$ alkoxyalkyl, $C_2$-$C_6$ alkylcarbonyl, $C_1$-$C_6$ alkylthio, $C_1$-$C_6$ haloalkyl, $C_1$-$C_6$ haloalkoxy, $C_2$-$C_4$ haloalkoxyalkyl, $C_2$-$C_6$ haloalkylcarbonyl, $C_1$-$C_6$ haloalkylthio, —OCH$_2$CH$_2$—, —OCH$_2$CH$_2$CH$_2$—, —OCH$_2$O—, or —OCH$_2$CH$_2$O—;
R represents H or F;
X represents Cl or vinyl;
Y represents Cl, vinyl or methoxy; and
their salts and esters;
comprising, with respect to the total composition, from about 1 gram per kilogram (g/kg) to about 200 g/kg;
  b) a built-in adjuvant comprising, with respect to the total composition, from about 50 g/kg to about 750 g/kg;
  c) a solid carbohydrate comprising, with respect to the total composition, from about 10 g/kg to about 700 g/kg; and
  d) a solid, water soluble polymer or oligomer comprising, with respect to the total composition, from about 50 g/kg to about 700 g/kg, with the proviso that the solid carbohydrate and the solid, water soluble polymer or oligomer must together comprise at least 200 g/kg of the total composition.

Another aspect of the present invention concerns a method of controlling undesirable vegetation in an aquatic environment by using the herbicidal solid compositions or spray solutions derived from the herbicidal solid compositions for agricultural applications such as for improved weed control in water flooded rice paddies and fields.

Another aspect of the present invention concerns a method of preparing the herbicidal solid composition which may be a granule or a powder.

DETAILED DESCRIPTION OF THE INVENTION

Agricultural active ingredients that have low water solubility can sometimes be difficult to effectively apply to crops to eliminate pests. This situation is particularly challenging when the active ingredients are not applied directly to plant foliage such as, for example, when herbicide granule products are used to control weeds in flooded paddy rice. Herbicide granules applied to flooded paddy rice are normally added directly to the water in the paddy rice and have very little direct contact with plant foliage during application. For example, cyhalofop-butyl is an herbicidal active ingredient that when applied to water in a granule, requires the use of a built-in adjuvant to provide the necessary delivery and uptake of the herbicide into the target weeds and expression of acceptable levels of weed control. Granules that are capable of containing high levels of built-in adjuvants can offer improved weed control in aquatic environments such as, for example, flooded paddy rice on a grams active ingredient per hectare (gai/ha) basis.

The solid compositions of the present invention are those solid agricultural compositions containing active ingredients and inert ingredients, and include granules, dispersible granules, emulsifiable granules, powders, wettable powders and the like.

Stable solid compositions are generally defined as those that are stable physically and chemically to the environments in which they are produced and stored. The stability includes the inhibition of leakage or loss of ingredients contained in the solid composition, particularly liquid ingredients such as a liquid active ingredient or a liquid built-in adjuvant.

The solid composition of the present invention may contain high levels of built-in adjuvant by the use of a combination of a solid carbohydrate and one or more of a solid, water soluble polymer or oligomer that together stabilize the solid composition during preparation and storage.

The solid composition of the present invention is comprised of an herbicide active ingredient, a built-in adjuvant, a solid carbohydrate and a solid, water soluble polymer or oligomer.

The herbicide active ingredient of the present invention may be selected from the ACCase (acetyl coenzyme A carboxylase) enzyme inhibitor class of herbicides or the ALS (acetolactate synthase) enzyme inhibitor class of herbicides. The ACCase inhibiting herbicide active ingredients which are known in the art as the "fop" and "dim" herbicides include, but are not limited to, cyhalofop-butyl, fenoxaprop-ethyl, fluazifop-P-butyl, haloxyfop-methyl, haloxyfop-R-methyl, metamifop, propaquizafop, quizalofop-P-ethyl, quizalofop-P-tefuryl and profoxydim. The ALS inhibiting herbicide active ingredients include, but are not limited to, azimsulfuron, bensulfuron-methyl, cloransulam-methyl, cyclosulfamuron, diclosulam, ethoxysulfuron, florasulam, flucetosulfuron, flumetsulam, halosulfuron-methyl, metazosulfuron, metosulam, metsulfuron, penoxsulam, primisulfuron-methyl, propyrisulfuron, pyrazosulfuron-ethyl, pyroxsulam, imazethapyr, imazamox, imazosulfuron and derivatives thereof. The herbicide active ingredient of the present invention generally has a water solubility of less than about 3000 parts per million (ppm), preferably less than about 1000 ppm and most preferably less than about 100 ppm at environmental pH conditions (pH of about 6.5 to about 7.5). The herbicide active ingredient comprises, with respect to the total composition, from about 1 g/kg to about 200 g/kg, preferably from about 2 g/kg to about 75 g/kg.

Additional herbicide active ingredients of the present invention include compounds of the Formula

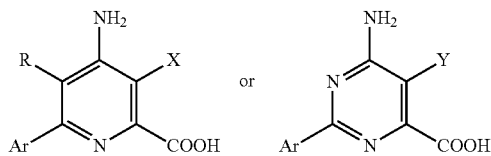

wherein

Ar represents a phenyl group substituted with one to four substituents independently selected from halogen, $C_1$-$C_6$ alkyl, $C_1$-$C_6$ alkoxy, $C_2$-$C_4$ alkoxyalkyl, $C_2$-$C_6$ alkylcarbonyl, $C_1$-$C_6$ alkylthio, $C_1$-$C_6$ haloalkyl, $C_1$-$C_6$ haloalkoxy, $C_2$-$C_4$ haloalkoxyalkyl, $C_2$-$C_6$ haloalkylcarbonyl, $C_1$-$C_6$ haloalkylthio, —OCH$_2$CH$_2$—, —OCH$_2$CH$_2$CH$_2$—, —OCH$_2$O—, or —OCH$_2$CH$_2$O—;

R represents H or F;

X represents Cl or vinyl; and

Y represents Cl, vinyl or methoxy;

and their salts and esters as disclosed, for example, in U.S. Pat. No. 7,314,849 B2, U.S. Pat. No. 7,300,907 B2, U.S. Pat. No. 7,786,044 B2 and U.S. Pat. No. 7,642,220 B2. An especially suitable herbicide of this class is the compound

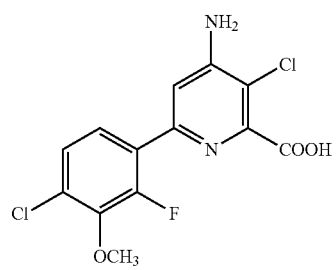 [SMILES: COc1c(Cl)ccc(-c2cc(N)c(Cl)c(C(=O)O)n2)c1F]

and its $C_1$-$C_6$ alkyl esters or salt derivatives such as, for example, the methyl ester which is referred to herein as Compound A.

The built-in adjuvant of the present invention can be in the form of a liquid or a solid and may include one or more of a non-ionic surfactant or a water immiscible liquid. Non-ionic surfactants that may be used as built-in adjuvants of the present invention include, but are not limited to, polyol fatty acid esters, polyethoxylated esters, polyethoxylated alcohols, alkyl polysaccharides such as alkyl polyglycosides and blends thereof, amine ethoxylates, sorbitan fatty acid ester ethoxylates, organosilicone based surfactants, ethylene vinyl acetate terpolymers, ethoxylated alkyl aryl phosphate esters and sucrose esters of fatty acids.

Water immiscible liquids that may be used as built-in adjuvants generally have less than about 1 volume per cent solubility in water and may include, but are not limited to, petroleum fractions or hydrocarbons such as mineral oil, kerosene, paraffinic oils, mixed naphthalene and alkyl naphthalene fractions, aromatic solvents, particularly alkyl substituted benzenes such as xylene or propylbenzene fractions, and the like; plant derived oils such as soybean oil, rape seed oil, olive oil, castor oil, sunflower seed oil, coconut oil, corn oil, cotton seed oil, linseed oil, palm oil, peanut oil, safflower oil, sesame oil, tung oil and the like; esters of the above plant derived oils such as 2-ethyl hexyl stearate, n-butyl oleate, isopropyl myristate, propylene glycol dioleate and the like; and esters of diacids such as di-octyl succinate, di-butyl adipate, di-octyl phthalate, ditridecyl phthalate and the like.

Preferred built-in adjuvants include one or more of petroleum fractions or hydrocarbons such as mineral oil, paraffinic oils and aromatic solvents like xylene, propylbenzene fractions, alkyl naphthalene fractions, and the like; plant derived oils such as soybean oil, rape seed oil, olive oil, castor oil, sunflower seed oil, coconut oil, corn oil, cotton seed oil, linseed oil, palm oil, peanut oil, safflower oil, sesame oil, tung oil and the like; $C_1$-$C_6$ esters of plant derived oils such as methylated seed oils; esters of diacids such as di-octyl succinate, di-butyl adipate, di-octyl phthalate, ditridecyl phthalate and the like; polyol fatty acid esters, polyethoxylated esters, polyethoxylated alcohols, alkyl polysaccharides such as alkyl polyglycosides and blends thereof, amine ethoxylates, sorbitan fatty acid ester ethoxylates, organosilicone based surfactants, ethylene vinyl acetate terpolymers, ethoxylated alkyl aryl phosphate esters and sucrose esters of fatty acids.

The built-in adjuvant of the present invention comprises, with respect to the total composition, from about 50 g/kg to about 750 g/kg, preferably from about 200 g/kg to about 600 g/kg and most preferably from about 300 g/kg to about 600 g/kg.

The solid carbohydrates of the present invention include monosaccharides, disaccharides or polysaccharides, and mixtures thereof, with good water solubility or dispersibility. The solid carbohydrates include, for example, glucose, fructose, sucrose, trehalose, lactose and maltose, dextrines, starches, modified starches, modified celluloses such as, for example, alkylated and carboxyalkylated celluloses, natural gums such as, for example, guar gums, xanthum gums and guaseed gums, and the like, and mixtures thereof. Preferred solid carbohydrates of the present invention are mono- and disaccharides.

The solid carbohydrate of the present invention may comprise, with respect to the total composition, from about 10 g/kg to about 700 g/kg, preferably from about 10 g/kg to about 500 g/kg and most preferably from about 10 g/kg to about 400 g/kg.

The solid, water soluble polymer or oligomer of the present invention includes one or more of a synthetic or partially synthetic polymer or oligomer that swells, disperses or dissolves in water at ambient temperature. Typical solid, water soluble polymers or oligomers include lignosulfonates, alkyl naphthalene sulfonate formaldehyde condensates, polyvinyl alcohols, polyacrylates, polyethylene oxides, polyvinylpyrrolidones and co-polymers, derivatives and mixtures thereof.

Preferred solid, water soluble polymers or oligomers of the present invention include polyvinyl alcohols derived from the hydrolysis of polyvinyl acetate, that vary in the degree of hydrolysis from about 87 to about 99%, of which Celvol® 205 (registered trademark of Sekisui Chemical Co., Ltd.) is an example, lignosulfonates of which Borresperse® NA (registered trademark of Borregaard LignoTech) is an example and alkyl naphthalene sulfonate formaldehyde condensates of which Morwet® D425 (registered trademark of Akzo Nobel) is an example, and co-polymers, derivatives and mixtures thereof.

The solid, water soluble polymer or oligomer of the present invention comprises, with respect to the total composition, from about 50 to about 700 g/kg, preferably from about 100 to about 600 g/kg, and most preferably from about 150 to about 600 g/kg, with the proviso that the solid carbohydrate and the solid, water soluble polymer or oligomer must together comprise at least 200 g/kg of the total composition.

In a typical procedure for preparing the solid composition of the present invention an aqueous phase is prepared by mixing in water the water soluble or water dispersible ingredients including, but not limited to, the solid water soluble polymer or oligomer, the solid carbohydrate and, optionally, any oil insoluble active ingredient and other inert ingredients. An oil phase is prepared by mixing together any oil soluble ingredients including, but not limited to, built-in adjuvants and oil soluble active ingredients. The oil phase is slowly added into the aqueous phase under high shear homogenization until the desired mixture is achieved. The mixture is then dried to provide the solid compositions as the granule directly or the drying may provide the powder of the present invention which, optionally, can be further processed to provide the granule of the present invention.

An example of a stable herbicidal solid composition of the present invention containing built-in adjuvant comprises:
 a) an herbicide active ingredient comprising, with respect to the total composition, from about 2 g/kg to about 75 g/kg of cyhalofop-butyl;
 b) a built-in adjuvant comprising, with respect to the total composition, from about 300 g/kg to about 600 g/kg of a methyl soyate;
 c) a solid carbohydrate comprising, with respect to the total composition, from about 10 g/kg to about 400 g/kg of sucrose;
 d) a solid, water soluble polymer or oligomer comprising, with respect to the total composition, from about 10 g/kg to about 100 g/kg of an 86-89% hydrolyzed polyvinyl alcohol;
 e) a solid, water soluble polymer or oligomer comprising, with respect to the total composition, from about 150 g/kg to about 600 g/kg of sodium lignosulfonate; and
 f) optionally, other inert formulation ingredients.

Another aspect of the present invention concerns a method of controlling weeds by broadcasting or adding the herbicidal solid composition or spraying an aqueous solution or mixture made from the herbicidal solid composition into aquatic environments such as rice paddies, ponds, lakes and streams and the like, for the control of undesirable vegetation. In this aspect a herbicidally effective amount of the herbicidal solid composition or an aqueous spray solution or mixture made from the herbicidal solid composition is applied to an area of water to provide suitable control of undesirable weed plants. The herbicidal solid composition or spray solutions made from the herbicidal solid composition are particularly useful for the control of grass, broadleaf and sedge-weeds in flooded rice paddies or fields.

An additional aspect of the present invention concerns a method of preparing the herbicidal solid compositions. Granule formulations may be produced using one or more of the following processing methods: (1) pan granulation, (2) mixing agglomeration, (3) extrusion granulation, (4) fluid bed granulation, (5) spray granulation or agglomeration and (6) drum granulation. Also, preparation of granules using a pellet press may be used. The physico-chemical properties of the active ingredient and additives are important to consider when choosing a process to use. G. A. Bell and D. A. Knowles in, "Chemistry and Technology of Agrochemical Formulations," D. A. Knowles, editor, (Kluwer Academic Publishers, 1998), pages 41-114, describe the types of granules used in agricultural chemical formulations and provide many references to the production of these solid formulations. Powder formulations can be produced by vacuum drying, rotary evaporator drying, spray drying, drum drying or other processing methods that are well known to those of normal skill in the art. In any of the processing methods described herein, optional inert ingredients may be added to the composition before, during or after processing to improve the processing or to improve the final quality or stability of the granule or powder. These optional inert ingredients may include, but are not limited to, flowability additives and anti-caking agents such as, for example, hydrophilic precipitated silicas, hydrophilic fumed silicas and clays, anti-foaming agents, wetting agents, binders, dispersing agents, solid diluents and carriers.

There are many examples where solid additives are used to stabilize water insoluble liquids during processing to make stable powders. Examples of such additives are gelatine, glycine, casein, water-soluble polymers such as polyvinyl alcohol and polyvinyl pyrrolidone, and polysaccharides. Some of these applications are described, for example, in U.S. Pat. No. 4,244,836 and WO 2006/076943. There have been, however, very limited efforts to stabilize built-in adjuvants during processing to produce agricultural granules or powders.

A method of preparing the stable herbicidal solid compositions of the present invention capable of containing high levels of built-in adjuvant comprises:
 (1) mixing all solid, water soluble polymers or oligomers and solid carbohydrate ingredients in water to form an aqueous phase;
 (2) mixing the built-in adjuvant and oil soluble or oil dispersible active ingredients to form an oil phase;
 (3) adding the oil phase prepared in step (2) to the aqueous phase prepared in step (1) under high shear homogenization to provide a mixture; and
 (4) drying the mixture prepared in (3) to provide the stable granule or powder of the present invention.

The most optimal way of practicing the method above to prepare the stable herbicidal solid compositions of the present invention can easily be determined by one of ordinary skill in the art.

A preferred method of preparing the stable herbicide granule or powder of the present invention capable of containing high levels of built-in adjuvant involves taking the mixture obtained in step 3 of the method of preparation described herein and spray drying it to provide the stable powder of the present invention which may then be further processed into the stable granule using a low-shear granulation method such as pan granulation, fluid bed agglomeration or spray agglomeration. Use of such low shear processing methods is necessary to minimize mechanical damage to the granule and loss of the built-in adjuvant.

Another aspect of the present invention concerns adding one or more pesticide active ingredients, plant growth regulators or safeners to the herbicidal solid compositions of the present invention. These pesticide active ingredients, plant growth regulators and safeners may include one or more of an herbicide, an insecticide, a fungicide, a plant growth regulator or an herbicide safener.

Suitable herbicides that may be added to the herbicidal solid compositions of the present invention include clodinafop-propargyl, clethodim, cycloxydim, diclofop-methyl, fenoxaprop-ethyl+isoxidifen-ethyl, pinoxaden, sethoxydim, tepraloxydim, tralkoxydim, 2,4-D esters and amines, 2,4-MCPA, 2,4-MCPA esters and amines, acetochlor, acifluorfen, alachlor, amidosulfuron, aminopyralid, aminotriazole, ammonium thiocyanate, anilifos, benfuresate, bentazon, bentazone-sodium, benthiocarb, benzobicyclon, benzofenap, bifenox, bispyribac-sodium, bromobutide, butachlor, cafenstrole, carfentrazone-ethyl, chlorimuron, chlorpropham, cinosulfuron, clomazone, clomeprop, clopyralid, cumyluron, daimuron, diflufenican, dimepiperate, dimethametryn, diquat, dithiopyr, EK2612, EPTC, esprocarb, ET-751, ethbenzanid, fenoxasulfone, fentrazamide, flazasulfuron, fluazifop, flufenacet, flufenpyr-ethyl, flumioxazin, flupyrsulfuron, fluroxypyr, fluroxypyr esters and salts, fomesafen, foramsulfuron, glufosinate, glufosinate-P, glyphosate, imazamethabenz, imazapic, imazapyr, imazaquin, indanofan, ioxynil, ipfencarbazone, isoxaben, MCPB, mefenacet, mesosulfuron, mesotrione, metolachlor, molinate, monosulfuron, MSMA, orthosulfamuron, oryzalin, oxadiargyl, oxadiazon, oxazichlomefone, oxyfluorfen, paraquat, pendimethalin, pentoxazone, pethoxamid, picloram, piperophos, pretilachlor, prohexadione-calcium, propachlor, propanil, propisochlor, propyzamide, prosulfuron, pyrabuticarb, pyraclonil, pyrazogyl, pyrazolynate, pyrazoxyfen, pyribenzoxim, pyridate, pyriftalid, pyriminobac-methyl, pyrimisulfan, quinoclamine, quinclorac, S-3252, simazine, simetryne, s-metolachlor, sulcotrione, sulfentrazone, sulfosate, tefuryltrione, thenylchlor, thiazopyr, thiobencarb, triafamone, triclopyr, triclopyr-esters and amines, trifluralin, trinexapac-ethyl and tritosulfuron.

Suitable insecticides that may be added to the herbicidal solid compositions of the present invention include abamectin, acephate, acetamiprid, acrinathrin, alpha-cypermethrin, alpha-endosulfan, azadirachtin, azinphos-ethyl, azinphos-methyl, bendiocarb, benfuracarb, bensultap, beta-cyfluthrin, beta-cypermethrin, bifenthrin, bufencarb, buprofezin, butacarb, cadusafos, carbaryl, carbofuran, carbosulfan, cartap, cartap hydrochloride, chlorantraniliprole, chlorfenapyr, chlorfenvinphos, chlorfluazuron, chlormephos, chlorpyrifos, chlorpyrifos-methyl, chromafenozide, clothianidin, cyantraniliprole, cyfluthrin, cyhalothrin, cypermethrin, deltamethrin, diazinon, dicrotophos, diflubenzuron, dimethoate dinotefuran, disulfoton, emamectin, emamectin benzoate, endosulfan, endothion, endrin, EPN, esfenvalerate, etaphos, ethiofencarb, ethion, ethiprole, ethoate-methyl, etofenprox, fenamiphos, fenazaflor, fenethacarb, fenitrothion, fenobucarb, fenpropathrin, fensulfothion, fenthion, fenthion-ethyl, fenvalerate, fipronil, flonicamid, flubendiamide, flucythrinate, fonofos, fufenozide, furathiocarb, gamma-cyhalothrin, gamma-HCH, halfenprox, halofenozide, heptenophos, hyquincarb, imidacloprid, indoxacarb, isazofos, isobenzan, isocarbophos, isofenphos, isofenphos-methyl, isoprocarb, isothioate, isoxathion, kinoprene, lambda-cyhalothrin, lepimectin, lufenuron, malathion, methamidophos, methomyl, methoxyfenozide, mevinphos, mexacarbate, milbemectin, monocrotophos, nitenpyram, novaluron, omethoate, oxamyl, oxydemeton-methyl, oxydeprofos, oxydisulfoton, parathion, parathion-methyl, penfluron, permethrin, phenthoate, phorate, phosalone, phosfolan, phosmet, phosphamidon, pirimetaphos, pirimicarb, pirimiphos-ethyl, pirimiphos-methyl, primidophos, profenofos, profluthrin, promecarb, propaphos, propoxur, prothiofos, pymetrozine, pyrafluprole, pyridalyl, pyrifluquinazon, pyriprole, pyriproxyfen, spinetoram, spinosad, spirotetramat, sulfoxaflor, sulprofos, tau-fluvalinate, tebufenozide, tebufenpyrad, teflubenzuron, tefluthrin, tetramethylfluthrin, theta-cypermethrin, thiacloprid, thiamethoxam, thicrofos, thiocyclam, thiocyclam oxalate, thiodicarb, thiometon, thiosultap, thiosultap-disodium, thiosultap-monosodium, thuringiensin, tolfenpyrad, triazophos, triflumuron and zeta-cypermethrin.

Suitable fungicides that may be added to the herbicidal solid compositions of the present invention include tricyclazole, phthalide, carpropamide, pyroquilon, diclocymet, fenoxanil, probenazole, isoprothiolane, iprobenfos, isotianil, tiadinil, kasugamycin, flutolanil, mepronil, pencycuron, polyoxins, validamycin, toclophos-methyl, boscalid, penthiopyrad, thifluzamide, bixafen, fluopyram, isopyrazam, propiconazole, difenoconazole, fenbuconazole, ipconazole, triadimefon, hexaconazole, azoxystrobin, metaminostrobin, orysastrobin and acibenzolar-S-methyl. Some of these fungicides may not be effective for disease control when applied at the timing of an herbicide granule application because fungal disease propagation and growth cycles may not match the targeted weed growth cycles. The effective use and application timing of these fungicides can be easily determined by one of normal skill in the art.

Suitable herbicide safeners that may be added to the herbicidal solid compositions of the present invention include benoxacor, benthiocarb, cloquintocet-mexyl, daimuron, dichlormid, dicyclonon, dimepiperate, fenchlorazole-ethyl, fenclorim, flurazole, fluxofenim, furilazole, Harpin proteins, isoxadifen-ethyl, mefenpyr-diethyl, mephenate, MG 191, MON 4660, naphthalic anhydride (NA), oxabetrinil, R29148 and N-phenyl-sulfonylbenzoic acid amides.

Suitable plant growth regulators that may be added to the herbicidal solid compositions of the present invention include 2,4-D, 2,4-DB, IAA, IBA, naphthaleneacetamide, α-naphthaleneacetic acid, kinetin, zeatin, ethephon, aviglycine, 1-methylcyclopropene (1-MCP), ethephon, gibberellins, gibberellic acid, abscisic acid, ancymidol, flurprimidol, mefluidide, paclobutrazol, tetcyclacis, uniconazole, brassinolide, brassinolide-ethyl and ethylene.

In addition to the compositions and uses set forth above, the present invention also embraces the composition and use of the herbicidal solid compositions in combination with one or more additional compatible ingredients. Other additional compatible ingredients may include, for example, one or more agrochemical active ingredients, surfactants, dyes, fertilizers and micronutrients, pheromones and many other additional ingredients providing functional utility, such as, for example, stabilizers, fragrants and dispersants. When the compositions of the present invention are used in combination with additional active ingredients the presently claimed compositions can be formulated with the other active ingredient or active ingredients as herbicidal solid compositions, tank mixed in water with the other active ingredient or active ingredients for spray application or applied sequentially with the other active ingredient or active ingredients in separate solid or spray applications.

In addition, the herbicidal solid compositions of the present invention may optionally be blended with other solid compositions containing additional active ingredients to form a composition containing, for example, a physically uniform blend of granules or a physically uniform blend of powders. This blend of solid compositions may be used to control undesirable weeds in aquatic environments such as flooded rice paddies and fields.

Surfactants conventionally used in the art of formulation and which may optionally be used in the present formulations are described, inter alia, in "McCutcheon's Detergents and Emulsifiers Annual", MC Publishing Corp., Ridgewood, N.J., 1998 and in "Encyclopedia of Surfactants", Vol. I-III, Chemical publishing Co., New York, 1980-81. These surface-active agents can be anionic, cationic or nonionic in character and can be employed as emulsifying agents, wetting agents, suspending agents, or for other purposes. Typical surface-active agents include salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ethoxylate; soaps, such as sodium stearate; alkylnaphthalene-sulfonate salts, such as sodium dibutyl-naphthalenesulfonate; dialkyl esters of sulfosuccinate salts, such as sodium di(2-ethylhexyl) sulfosuccinate; quaternary amines, such as lauryl trimethylammonium chloride; block copolymers of ethylene oxide and propylene oxide; salts of mono and dialkyl phosphate esters.

Oftentimes, some of these surfactants can be used interchangeably as an agricultural adjuvant, as a liquid carrier or as a surface active agent.

The following examples illustrate the present invention.

Example 1

Preparation of Granules of the Present Invention Containing Cyhalofop-Butyl that are Oven Dried on a Flat Pan An oil phase is prepared by dissolving 1.8 grams of cyhalofop-butyl in 43.2 grams of methyl soyate (Agnique® ME 18S-U; registered trademark of Cognis). An aqueous phase is prepared by dissolving 32 grams of sucrose, 10 grams of a 20% (w/w) solution of Celvol® 205 (polyvinyl alcohol; trademark of Sekisui Chemical Co., Ltd.) in water, and 21 grams of sodium lignosulfonate (Borresperse° NA; registered trademark of Borregaard LignoTech) in 71 grams of water. The oil phase is then slowly added to the aqueous phase while mixing with a Silverson high shear mixer for 30 minutes at approximately 11,000 rpm to produce a mixture of dispersed oil droplets in water with a volume mean diameter of about 1-2 microns. Once the desired droplet size is obtained, the mixture is dried in a flat dish in an oven at 60° C. to provide a dried solid of Granule A (Table 1) with a residual water content of from about 2 to about 3 weight percent with respect to the total sample weight. The volume mean diameter of the solid particles produced from Granule A ranges from about 2 to about 4 microns upon re-dispersion in water. In a similar manner to that described herein Granules B and C (Table 1) were also prepared.

TABLE 1

Composition of Granules of the Present Invention

| Ingredients | Granule A Wt % | Granule B Wt % | Granule C Wt % |
|---|---|---|---|
| cyhalofop-butyl | 1.8 | 3.6 | 5.4 |
| methyl soyate | 43.2 | 41.4 | 39.6 |
| sucrose | 32 | 32 | 32 |
| Borresperse ® NA | 21 | 21 | 21 |
| Celvol ® 205 | 2 | 2 | 2 |

Example 2

Preparation of Granules of the Present Invention Containing Penoxsulam, Bensulfuron-methyl, Fenoxaprop-P-ethyl, Compound A, Azimsulfuron or Imazosulfuron Granules D, E and G:

Using the ingredients shown in Table 2, aqueous suspension concentrates (SC) containing the active ingredients are prepared by overnight shaking of 25% solids solutions containing the technical active ingredient, Morwet D425 and Pluronic P105 in 20 ml plastic bottles in the weight proportions shown in Table 2 and containing steel beads of 9-10 times the weight of the 25% solids solutions. An aqueous phase is prepared by dissolving 1 gram of sucrose, 10 grams of a 20% (w/w) solution of Celvol® 205 (polyvinyl alcohol; trademark of Sekisui Chemical Co., Ltd.) in water, and ~51.7 gram of sodium lignosulfonate (Borresperse® NA; registered trademark of Borregaard LignoTech) in 96 grams of water. The oil phase (e.g. 44 grams of methyl soyate—Agnique® ME 18S-U; registered trademark of Cognis) is then slowly added to the aqueous phase while mixing with a Silverson high shear mixer for 30 minutes at approximately 11,000 rpm to produce a mixture of dispersed oil droplets in water with a volume mean diameter of about 1-3 microns. Once the desired droplet size is obtained, the suspension concentrate of active ingredient is added into the mixture to prepare the final aqueous mixture containing 1 gram of active ingredient. Upon gentle mixing at low shear (1000 to 2000 rpm) using a Silverson or IKA mixer, the aqueous mixture is spray dried in a BUCHI 190 spray dryer with an inlet temperature of 135° C. and outlet temperature of 90° C. with a feed rate of 300 ml/hr to provide solid powder with a residual water content of from about 2 to about 3 weight percent with respect to the total sample weight. The spray dried powder is granulated using a kitchen mixer (Black & Decker Handy Chopper HC2000) and 12 wt % of water as the binder. The kitchen mixer blades are wrapped with plastic tape to reduce the shear exerted by the blades on the spray dried powder. Final product is obtained by drying the granules at 30 to 50° C. until the overall moisture level reaches about 3% of the sample weight.

Granule F:

Using the ingredients shown in Table 2, an aqueous phase is prepared by dissolving 1 gram of sucrose, 10 grams of a 20% (w/w) solution of Celvol® 205 (polyvinyl alcohol; trademark of Sekisui Chemical Co., Ltd.) in water, and 51.95 gram of sodium lignosulfonate (Borresperse® NA; registered trademark of Borregaard LignoTech) in 96.5 grams of water. An oil phase is prepared by dissolving 1 gram of fenoxaprop-P-ethyl in 44 grams of methyl soyate (Agnique® ME 18S-U; registered trademark of Cognis). The oil phase is then slowly added to the aqueous phase while mixing with a Silverson high shear mixer for 30 minutes at approximately 11,000 rpm to produce a mixture of dispersed oil droplets in water with a volume mean diameter of about 1-3 microns. Once the desired droplet size is obtained, the aqueous mixer is spray dried in a BUCHI 190 spray dryer with inlet temperature of 135° C. and outlet temperature of 90° C. with a feed rate of 300 ml/hr to provide a solid powder with a residual water content of about 2 to 3 weight percent with respect to the total sample weight. The powder is granulated using the kitchen mixer described herein and 12 wt % of water as a binder. The kitchen mixer blades are wrapped with plastic tape to reduce the shear exerted by the blades on the spray dried powder. Final product is obtained by drying the granules at 30 to 50° C. until the overall moisture level reaches about 3% of the sample weight.

Granules H and I:

Using the ingredients shown in Table 2, suspension concentrates containing the active ingredients are prepared by mixing 2 grams of 50 wt % active ingredients commercial granules (e.g. Brazzos WG and Gulliver WG formulations) in 8 grams of water to prepare ~20% solids solutions of each, respectively. An aqueous phase is prepared by dissolving 1 gram of sucrose, 10 grams of a 20% (w/w) solution of Celvol® 205 (polyvinyl alcohol; trademark of Sekisui Chemical Co., Ltd.) in water, and ~51 gram of sodium lignosulfonate (Borresperse® NA; registered trademark of Borregaard LignoTech) in 95 grams of water. The oil phase (e.g. 44 grams of methyl soyate—Agnique® ME 18S-U; registered trademark of Cognis) is then slowly added to the aqueous phase while mixing with a Silverson high shear mixer for 30 minutes at approximately 11,000 rpm to produce a mixture of dispersed oil droplets in water with a volume mean diameter of about 1-3 microns. Once the desired droplet size is obtained, the suspension concentrate of active ingredients are added into the mixture to prepare final aqueous mixture containing 1 grams of active ingredient. Upon gentle mixing at low shear (1000 to 2000 rpm) under Silverson or IKA mixer, the aqueous mixer is spray dried in BUCHI 190 spray dryer with inlet temperature of 135° C. and outlet temperature of 90° C. with feed rate of 300 ml/hr to provide solid powder with a residual water content of from about 2 to about 3 weight percent with respect to the total sample weight. The powder is granulated using the kitchen mixer described herein and 12 wt % of water as a binder. The kitchen mixer blades are wrapped with plastic tape to reduce the shear exerted by the blades on the spray dried powder. Final product is obtained by drying granules at 30 to 50° C. until the overall moisture level reaches about 3% of the sample weight.

TABLE 2

Ingredients Used to Prepare Granules of the Present Invention Containing Penoxsulam, Bensulfuron-methyl, Fenoxaprop-P-ethyl, Compound A, Azimsulfuron and Imazosulfuron

| | Granule ID | | | | | |
|---|---|---|---|---|---|---|
| Ingredients | D Wt % | E Wt % | F Wt % | G Wt % | H[1] Wt % | I[1] Wt % |
| penoxsulam | 1 | 0 | 0 | 0 | 0 | 0 |
| bensulfuron-methyl | 0 | 1 | 0 | 0 | 0 | 0 |
| fenoxaprop-P-ethyl | 0 | 0 | 1 | 0 | 0 | 0 |
| Compound A | 0 | 0 | 0 | 1 | 0 | 0 |
| azimsulfuron | 0 | 0 | 0 | 0 | 1 | 0 |
| imazosulfuron | 0 | 0 | 0 | 0 | 0 | 1 |
| methyl soyate | 44 | 44 | 44 | 44 | 44 | 44 |
| sucrose | 1 | 1 | 1 | 1 | 1 | 1 |
| Borresperse NA[2] | 51.77 | 51.77 | 51.95 | 51.78 | 52 | 52 |
| Celvol 205 | 2 | 2 | 2 | 2 | 2 | 2 |
| Morwet D425 | 0.09 | 0.09 | 0 | 0.09 | 0 | 0 |
| Pluronic P105 | 0.14 | 0.14 | 0 | 0.13 | 0 | 0 |

[1]Granules H and I were prepared from the 50 wt % WG products Brazzos herbicide (Spiess-Urania) and Gulliver herbicide (Du Pont), respectively, and contain inert ingredients from those commercial products.
[2]Borresperse NA (sodium lignosulfonate) serves as the balance ingredient.

Example 3

Preparation of Granules and Powders of the Present Invention Containing Cyhalofop-Butyl Spray Dried Powder:

Using the ingredients and relative amounts shown in Table 3, four spray dried powders of the present invention are prepared as described. The oil phase of an oil-in-water emulsion is prepared by dissolving cyhalofop-butyl in methyl soyate in the desired proportions. An aqueous phase 3 times the weight of the oil phase is prepared by dissolving sucrose, a 20% aqueous solution of polyvinyl alcohol (Celvol® 205; Sekisui Chemical Co., Ltd.) and sodium lignosulfonate (Borresperse® NA; Lignotech, Inc.) in water. The oil phase is slowly added to the aqueous phase while mixing with a Silverson high shear mixer for 30 minutes at approximately 11,000 rpm to produce a fine emulsion containing oil droplets with a volume mean diameter of about 1-2 micrometers ($\mu m$). Once the desired emulsion size is obtained, the oil-in-water emulsion is dried using a spray dryer (Buchi Model 290) operated with inlet and outlet temperatures of about 135 and 85° C. each, respectively, and with a liquid feed rate of 300 mL/hr. The volume mean diameter of the dried powder obtained from the spray drying ranges from about 2 to 4 $\mu m$ upon re-dispersion in water. The spray dried powder disintegrates fairly quickly (in about 1 min) in water due to immediate dissolution of the sucrose and sodium lignosulfonate.

TABLE 3

Composition of Powders of the Present Invention Prepared by Spray Drying

| | Sample ID | | | |
|---|---|---|---|---|
| Ingredients | Powder A Wt % | Powder B Wt % | Powder C Wt % | Powder D Wt % |
| Cyhalofop Butyl | 1.35 | 2.7 | 1.35 | 1.80 |
| Impurity in technical | 0.05 | 0.1 | 0.05 | 0.07 |
| Methyl soyate | 43.6 | 42.2 | 43.6 | 43.13 |
| Sucrose | 32 | 32 | 10 | 1 |
| Sodium lignosulfonate | 21 | 21 | 43 | 52 |
| Polyvinyl alcohol | 2 | 2 | 2 | 2 |

Granules Prepared by Low-Shear Granulation:

A Ferro-tech (16" diameter) pan granulator was used for pan granulation. Two kilograms (kg) of spray dried Powder C was charged to the pan with a feed rate of 200 g/min The pan angle was set at 45° and the pan speed was set at 26 rpm. Water was continuously sprayed onto the powder while rotating the pan so that the final moisture content in the prepared granules is about 6 wt %. The prepared granules were then dried in a tray oven at 40° C. overnight and then sieved through a sieve stack to remove fines and any oversized granules. No oil separation was detected during the granulation process. The dried granules remain stable during storage stability testing at 54° C. for 4 weeks and do not show significant emulsion size change upon re-dispersion in water before and after storage stability testing. There was no caking or oil separation observed during the stability studies. The granules show good flowability and the flow characteristics remain unchanged after storage stability testing. The granules show good re-dispersibility upon dilution in water and disperse in 3 minutes without any agitation. The granules also show similar re-dispersibility after storage at 54° C. for 4 weeks. Up to about 5 wt % of hydrophilic silica can be used as a processing additive to improve the flowability/anti-caking of the final granules. The granules listed in Table 4 were prepared by low shear pan granulation in a similar manner to that described herein.

TABLE 4

Composition of Granules of the Present Invention Prepared by Low Shear Pan Granulation

| | Sample ID | | |
|---|---|---|---|
| Ingredients | Granule J Wt % | Granule K Wt % | Granule L Wt % |
| Cyhalofop Butyl | 1.80 | 3.6 | 5.4 |
| Impurity in technical | 0.07 | 0.13 | 0.2 |
| Methyl soyate | 43.13 | 41.27 | 39.4 |
| Sucrose | 1 | 1 | 1 |
| Sodium lignosulfonate | 52 | 52 | 52 |
| Polyvinyl alcohol | 2 | 2 | 2 |

Granules Prepared by Fluid Bed Agglomeration:

A pilot scale GPCG-1 Fluid Bed Granulator (manufactured by Glatt) was used for granulation processing. 800 g of Powder C was charged to the bowl of the granulator. The water spray rate was set to 15 g/min The inlet air temperature set point was set to 30° C. Water was sprayed for 5 minutes at 15 g/min The water spray rate was then reduced to 13 g/min and continued until a water content equal to 400 grams accumulated in the agglomerates. The agglomerates were dried with an inlet air temperature of 40° C. for a total time of 8 minutes and then unloaded. The granules obtained were sieved through a sieve stack of 12, 14, 20, 30 and 50 mesh sieves. Preferred sizes of −12/+14 mesh and −14/+20 mesh fractions were collected. The yield of +50 mesh fraction was significantly lower in comparison to −12/+14 mesh fraction indicating successful agglomeration. No oil exudation from the granules was observed. The granules can be further dried in an oven to a desired moisture level prior to storage.

Granules Prepared by Fluid Bed Spray Agglomeration:

Using an Aeromatic MP 1 Fluid Bed Multi-Processor (GEA Pharma Systems; bottom diameter 20 cm) with a nozzle at position 4 (70 cm above sieve), a spray rate of 25 g/min and a fluid bed temperature of about 68° C., a sample of 3 kg of Granule K were produced from an aqueous mixture containing 48.6 wt % solids that have the composition described in Table 4 (for Granule K). The granules produced had a bulk density of 580 grams/liter with 78.4 wt % of the granules having a size >1250 µm.

Example 4

Use of Granules A, B and C for Weed Control in Simulated Rice Paddys

Simulated Rice Paddies Preparation:

Two kg of mineral soil and 500 ml of distilled water were added to the container (4.163 L (1.1 gallon), 15 cm ht×20.55 cm diameter, HDPE round container; for treatment purposes the surface area is calculated as 331 cm$^2$ with 1 hectare equivalent to 10$^8$ cm$^2$) and thoroughly mixed with a spatula for about 5 minutes to create a smooth mud mix. Once the mud is mixed, a 3 cm. furrow is made across the middle of the container to which is added 18 g (0.6 oz.) Osmocote® (registered trademark of The Scotts Company LLC or its affiliates; 17:6:10 N:P:K). The furrow is then sealed keeping the Osmocote® below the surface of the soil.

Plant Propagation

Weed Plant

Chinese sprangletop, *Leptochloa chinensis* (LEFCH): In a small container, 80 grams of mineral soil is mixed with 40 milliliters (mL) of distilled water to make a viscous slurry. ¼ tsp (2-4000) of Leptochloa seed is added to the slurry and thoroughly mixed to evenly distribute the seed. Approximately 3 grams of this slurry is placed atop the prepared mud on one side of each container and spread thinly in a 1-2 cm band across the container. This yields 25-50 plants per pot. Clear shrink wrap is used to cover the containers acting as a terrarium. The wrap is held in place by masking tape until the Leptochloa seed germinates, about 5 days. The covered pots are kept in the greenhouse at a constant temperature of 18 to 22° C. and 50 to 60% relative humidity. Natural light was supplemented with 1000-watt metal halide overhead lamps with an average illumination of 500 microEinsteins per square meter per second ($\mu E\ m^{-2}\ s^{-1}$) photosynthetic active radiation (PAR). Day length was 16 hours.

Weed Plant

Barnyard grass, *Echinochloa crus-galli* (ECHCG): Once the sprangletop seed has germinated, a shallow depression is made in the mud parallel to the sprangletop. Barnyard grass seed is sprinkled along this trench and then covered with white play sand. This yields approximately 20-30 plants per pot. At this stage, the plant material is top-watered with distilled water and kept very moist. Pots are moved to a warmer greenhouse where the temperature is kept at 26 to 28° C. with the same lighting parameters as described for the Chinese sprangletop.

Crop Plant

Paddy rice, *Oryza sativa* subsp. *japonica* var. M202 (ORYSJ): On the same day that the barnyard grass is planted, the rice is also directly seeded into the pot mud following the same methodology. A shallow depression is made in the mud parallel to the Chinese sprangletop and Barnyard grass and the seed is sprinkled along this trench then covered with white play sand. This should also yield approximately 20-30 plants per pot.

The plants are allowed to grow until they reach 6-8 cm height in about 8 days.

Flooding and Paddies Application Methods for Herbicide Evaluations

Once the plants have reached the proper size (the growth stage of the various species ranged from 2 to 4 leaves) the containers are flooded with distilled water to a depth of 3 cm leaving 1-2 cm of each plant above the surface. Herbicide treatments are applied directly to the paddy water as granular or liquid formulations at rates adjusted to the surface area. Treatments were replicated 2-3 times. At intervals, percent visual injury and weed control assessments were made on a scale of 0 to 100% compared to the untreated control plants (where 0 is equal to no injury or control and 100 is equal to complete death of the plant).

TABLE 5

Crop Tolerance and Percent Weed Control with Cyhalofop-butyl Granules of the Present Invention 21 days After Application in a Simulated Rice Paddies Trial in the Greenhouse

| Herbicide Active Ingredient (ai) | Treatment Description | Application Rate (g ai/ha) | Average % Injury to Plants | | |
|---|---|---|---|---|---|
| | | | ORYSJ | LEFCH | ECHCG |
| cyhalofop-butyl | Granule A | 45 | 0 | 0 | 89 |
| | | 90 | 0 | 15 | 100 |
| | | 180 | 0 | 63 | 100 |
| | | 360 | 0 | 100 | 100 |
| cyhalofop-butyl | Granule B | 45 | 0 | 20 | 95 |
| | | 90 | 0 | 40 | 90 |
| | | 180 | 0 | 40 | 98 |
| | | 360 | 0 | 90 | 100 |
| cyhalofop-butyl | Granule C | 45 | 0 | 30 | 92 |
| | | 90 | 0 | 95 | 85 |
| | | 180 | 0 | 100 | 100 |
| | | 360 | 0 | 100 | 100 |
| cyhalofop-butyl | Clincher ®CA[1] | 45 | 0 | 5 | 5 |
| | | 90 | 0 | 10 | 10 |
| | | 180 | 0 | 40 | 45 |
| | | 360 | 0 | 95 | 75 |

[1]Clincher ®CA (registered trademark of Dow AgroSciences LLC) is an EC formulation containing 285 grams per liter of cyhalofop-butyl Example 5

Use of Granules of the Present Invention Containing Penoxsulam, Bensulfuron-Methyl, Fenoxaprop-P-Ethyl, Compound a, Azimsulfuron or Imazosulfuron for Weed Control in Simulated Rice Paddies Simulated Rice Paddies Preparation:

Add deionized (DI) water and shredded topsoil to a standard cement mixer in about a 1:1 volumetric ratio and mix well to create a smooth mud mixture. The mud moisture content may be checked in the following manner by using a 15 centimeter (cm) in diameter circular piece of a flat, non-absorbent hard plastic material. Place 380 ml of mud in the center of the plastic circle. Mud at the desired moisture content should spread to perfectly inscribe the circle. If the mud spreads beyond the circle's perimeter, it is too moist, and more topsoil must be added to the mud. If the mud does not spread to fully inscribe the circle, it is too dry and more DI water must be added to the mud. Adjust the topsoil to water ratio until the correct moisture content is achieved as described. 1½ Teaspoons of Osmocote® (registered trademark of The Scotts Company LLC or its affiliates; 17:6:10 N:P:K) are added to the bottom of a container (4.163 L (1.1 gallon), 15 cm ht×20.55 cm diameter, HDPE round container; for treatment purposes the surface area is calculated as 331 $cm^2$ with 1 hectare equivalent to $10^8$ $cm^2$) and then 2,750 ml of the mud mixture is added to the container filling it half full. Stakes are placed horizontally in each container to create separate areas for which to plant each different plant species.

Plant Propagation

Weed Plant

Monochoria, *Monochoria vaginalis* (MOOVA): In a small container, 80 grams of mineral soil is mixed with 80 milliliters (mL) of deionized water to make a viscous slurry. ½ tsp of Monochoria seed is added to the slurry and thoroughly mixed to evenly distribute the seed. Approximately 3 grams of this slurry is placed atop the prepared mud on one section of each container and spread thinly in a 1-2 cm band across the container. This yields 30-50 plants per pot. Clear shrink wrap is used to cover the containers acting as a terrarium. The wrap is held in place by masking tape until the Monochoria seeds germinate, about 7 days. The covered pots are kept in the greenhouse at a constant temperature of 28-32° C. and 50 to 60% relative humidity. Natural light was supplemented with 1000-watt metal halide overhead lamps with an average illumination of 500 µE $m^{-2}$ $s^{-1}$ photosynthetic active radiation (PAR). Day length was 16 hours.

Weed Plant

Barnyardgrass, *Echinochloa crus-galli* (ECHCG): The barnyardgrass is soaked in DI water for 24 hours, rinsed, and drained before planting to remove growth inhibitors and enhance germination. Once the monochoria seed has germinated, Barnyardgrass seed is sprinkled in its designated section, covered with 2 cm of 18 mesh fine sifted mineral soil, and labelled for identification. This yields approximately 20-30 plants per pot. At this stage, the plant material is covered with clear shrink wrap acting as a terrarium until the plants begin to germinate. The cover is removed once the barnyardgrass begins to emerge. Plants are reared in a greenhouse where the temperature is kept at 28-32° C. with the same lighting parameters as described for the monochoria. The plants are allowed to grow until they reach 5-9 cm height in about 8 days.

Weed Plant

Jungle rice, *Echinochloa colonum* (ECHCO): The Jungle rice is soaked in DI water for 24 hours, rinsed, and drained before planting to remove growth inhibitors, and enhance germination. Once the monochoria seed has germinated, Jungle rice seed is sprinkled in its designated section, covered with 2 cm of 18 mesh fine sifted mineral soil and labeled for identification. This yields approximately 20-30 plants per pot. At this stage, the plant material is covered with clear shrink wrap acting as a terrarium until the plants begin to germinate. The cover is removed once the jungle rice begins to emerge. Plants are reared in a greenhouse where the temperature is kept at 28 to 32° C. with the same lighting parameters as described for the monochoria and barnyardgrass. The plants are allowed to grow until they reach 5-9 cm height in about 8 days.

Flooding and Paddy Application Methods for Herbicide Evaluations

Once the plants have reached the proper size (the growth stage of the various species ranged from 2 to 4 leaves) the containers are flooded with deionized water to a depth of 3 inches submerging plants 80-100%. The outside of each container is measured and marked at a 3" flood line with a black permanent marker to eliminate water level variability. The granules are pre weighed based on the rate of the active ingredient to be applied on a per unit area basis, placed in 30 ml vials, and capped. Herbicide treatments are applied directly to the paddy water as granular formulations. Treatments were replicated 3 times. Percent visual injury and weed control assessments were made on a scale of 0 to 100% at the specified number of days after application by comparison to the untreated control plants (where 0 is equal to no injury or control and 100 is equal to complete death of the plant).

TABLE 6

Percent Weed Control with Granules of the Present Invention 21 Days after Application in a Simulated Rice Paddy Trial in the Greenhouse

| Herbicide Active Ingredient (ai) | Treatment Description | Application Rate (g ai/ha) | Average % Control | | |
|---|---|---|---|---|---|
| | | | MOOVA | ECHCG | ECHCO |
| penoxsulam | Granule D | 10 | 100 | 73 | 77 |
| | | 20 | 100 | 92 | 87 |
| bensulfuron-Me | Granule E | 17.5 | 98 | 13 | 30 |
| | | 35 | 99 | 75 | 55 |
| | | 70 | 100 | 85 | 70 |
| fenoxaprop-P-Et | Granule F | 21.5 | 1 | 58 | 100 |
| | | 43 | 8 | 100 | 100 |
| | | 86 | 82 | 100 | 100 |
| Compound A | Granule G | 25 | 100 | 28 | 70 |
| | | 50 | 100 | 90 | 100 |
| | | 100 | 100 | 100 | 100 |
| cyhalofop-butyl | XGA-2444[1] | 75 | 0 | 52 | 57 |
| | | 150 | 0 | 80 | 77 |
| | | 300 | 10 | 100 | 100 |

[1]XGA-2444 is a KCl granule formulation containing 18 g/kg of cyhalofop-butyl and 115 g/kg of the petroleum derived adjuvant ditridecyl phthalate (Clincher ®1KG from Nippon Kayaku Co., Ltd. of Japan)

TABLE 7

Percent Weed Control with Granules of the Present Invention 15 Days after Application in a Simulated Rice Paddy Trial in the Greenhouse

| Herbicide Active Ingredient (ai) | Treatment Description | Application Rate (g ai/ha) | Average % Control | |
|---|---|---|---|---|
| | | | MOOVA | ECHCG |
| azimsulfuron | Granule H | 17.5 | nt[1] | 72 |
| | | 35 | nt[1] | 94 |
| imazosulfuron | Granule I | 45 | 95 | 96 |
| | | 90 | 90 | 98 |

[1]nt = no test conducted

Example 6

Use of Granules of the Present Invention Containing Cyhalofop-Butyl for Weed Control in Rice Paddies in the Field Field trials were conducted in rice using standard herbicide small plot research methodology. Plot size was 2 m² using 1.6-m-diameter rings placed into the paddy soil with capability for flooding. There were 3 replicates per treatment. The rice crop was grown using normal cultural practices for fertilization, seeding, watering, flooding and maintenance to ensure good growth of the crop and the weeds under seeded rice conditions in Taiwan.

Rice was Japonica type that was sown directly into the rice paddy soil rings. Ring plot water was kept under saturated soil condition before treatment application. When treatment application was conducted, ring plot water was induced to 3 to 7 cm depth. The application timing was at 1 to 3 leaf stages of barnyardgrass. Treatment applications were calculated based on specific use rates on an area basis. Treatments were applied into the rice paddy soil rings by hand and ring plot water was maintained at 3 to 7 cm depth after treatment application. Treatments were rated as compared to the untreated control plots. Visual weed control was scored on a scale of 0 to 100 percent where 0 corresponds to no injury and 100 corresponds to complete kill.

Table 8 shows the biological efficacy of broadcast applications of the various treatments applied directly to the paddy water as granular formulations. The trial was conducted on paddy rice (ORYSW), sprangletop (LEFCH) and barnyard grass (ECHCG) and used various application rates of cyhalofop-butyl. A comparison treatment using a commercial granule formulation of cyhalofop-butyl (Clincher® 1 KG) was included in this flooded rice paddy field trial. The application rates are based on the grams of active ingredient per hectare (gai/ha) applied.

TABLE 8

Crop Tolerance and Percent Weed Control using Granules of the Present Invention - 28 Days after Application in a Rice Paddy Trial in the Field

| Herbicide Active Ingredient (ai) | Treatment Description | Application Rate (gai/ha) | Average % Injury to Plants | | |
|---|---|---|---|---|---|
| | | | ORYSW | LEFCH | ECHCG |
| cyhalofop-butyl | Granule J | 100 | 0 | 100 | 99 |
| | | 150 | 0 | 100 | 100 |
| | | 225 | 0 | 100 | 100 |
| | | 300 | 0 | 100 | 100 |
| cyhalofop-butyl | Granule K | 100 | 0 | 99 | 85 |
| | | 150 | 0 | 100 | 92 |
| | | 225 | 0 | 100 | 100 |
| | | 300 | 0 | 100 | 100 |
| cyhalofop-butyl | Granule L | 100 | 0 | 93 | 13 |
| | | 150 | 0 | 97 | 30 |
| | | 225 | 0 | 99 | 94 |
| | | 300 | 0 | 100 | 96 |
| cyhalofop-butyl | XGA-2444[1] | 100 | 0 | 95 | 85 |
| | | 150 | 0 | 97 | 90 |
| | | 225 | 0 | 100 | 94 |
| | | 300 | 0 | 100 | 98 |

[1]XGA-2444 is a KCl granule formulation containing 18 g/kg of cyhalofop-butyl and 115 g/kg of the petroleum derived adjuvant ditridecyl phthalate (Clincher ®1KG from Nippon Kayaku Co., Ltd. of Japan).

Example 7

Use of Powders of the Present Invention for the Preparation of Aqueous Spray Mixtures and their Use in Foliar Spray Applications to Control Weeds in Rice Paddies in the Field Field trials were conducted in rice using standard herbicide small plot research methodology. Plot size was 1 m² using 0.56 meter diameter rings placed into the paddy soil with capability for flooding with water. There were 3 replicates per treatment. The rice crop was grown using normal cultural practices for fertilization, seeding, watering, flooding and maintenance to ensure good growth of the crop and the weeds under seeded rice conditions in Taiwan. Rice was Japonica type that was sown directly into the rice paddy soil rings. Ring plot water was kept under saturated soil condition before foliar application. The application timing was at 3 to 4 leaf stages of barnyard grass. Treatments were applied by broadcasting foliar treatments with a backpack sprayer under compressed air at 30 psi pressure. Two nozzle booms using TEE JET-1101LP with a 50-cm distance were used for foliar application to cover each whole ring plot. Application volume was at 450 liters/hectare (L/Ha). Treatment applications were calculated based on specific use rates on an area basis. Ring plot water was re-introduced to 7 to 10 cm depth 24 hours after foliar application.

Table 9 shows the biological efficacy of spray applications using aqueous spray mixtures prepared from Powder A and Powder B. The trial was conducted on paddy rice (ORYSJ), sprangletop (LEFCH) and barnyard grass (ECHCG) and used various application rates of cyhalofop-butyl. A comparison treatment using a commercial EC formulation of cyhalofop-butyl (Clincher® 100EC) was included in this flooded rice paddy field trial. The application rates are based on the grams of active ingredient per hectare (gai/ha) applied.

TABLE 9

Crop Tolerance and Percent Weed Control with Cyhalofop-butyl Aqueous Spray Mixtures Prepared from Powders of the Present Invention, 15 days After Foliar Application in a Flooded Rice Paddy Field Trial.

| Herbicide Active Ingredient (ai) | Treatment Description | Application Rate (g ai/ha) | Average % Injury to Plants | | |
|---|---|---|---|---|---|
| | | | ORYSJ | LEFCH | ECHCG |
| cyhalofop-butyl | Powder A | 45 | 0 | 0 | 0 |
| | | 90 | 0 | 80 | 7 |
| | | 180 | 0 | 97 | 87 |
| | | 360 | 0 | 100 | 99 |
| cyhalofop-butyl | Powder B | 45 | 0 | 0 | 0 |
| | | 90 | 0 | 47 | 7 |
| | | 180 | 0 | 92 | 63 |
| | | 360 | 0 | 98 | 95 |
| cyhalofop-butyl | Clincher ®100EC[1] | 45 | 0 | 0 | 0 |
| | | 90 | 0 | 60 | 0 |
| | | 180 | 0 | 95 | 17 |
| | | 360 | 0 | 99 | 97 |

[1]Clincher ® 100EC (registered trademark of Dow AgroSciences LLC) is an EC formulation containing 100 grams per liter of cyhalofop-butyl.

What is claimed:

1. A stable herbicide granule containing built-in adjuvant which comprises:
   a) an herbicide active ingredient selected from the class of ACCase or ALS enzyme inhibitors comprising, with respect to the total composition, from about 1 gram per kilogram (g/kg) to about 200 g/kg;
   b) a built-in adjuvant comprising, with respect to the total composition, from about 50 g/kg to about 750 g/kg, wherein the built-in adjuvant is one or more of a nonionic surfactant or a water immiscible liquid;
   c) a solid carbohydrate comprising, with respect to the total composition, from about 10 g/kg to about 700 g/kg, wherein the solid carbohydrate is a monosaccharide, a disaccharide, or a polysaccharide, or a mixture thereof; and
   d) a solid, water soluble polymer or oligomer comprising, with respect to the total composition, from about 50 g/kg to about 700 g/kg, with the proviso that the solid carbohydrate and the solid, water soluble polymer or oligomer must together comprise at least 200 g/kg of the total composition;
   wherein the herbicide active ingredient has a water solubility of less than or about 3000 parts per million at pH of about 6.5 to about 7.5.

2. A method of preparing the stable herbicide granule of claim 1, which comprises:
   a) mixing all solid, water soluble polymers or oligomers and solid carbohydrate ingredients in water to form an aqueous phase;
   b) mixing the built-in adjuvant and oil soluble or oil dispersible active ingredients to form an oil phase;
   c) adding the oil phase prepared in step b) to the aqueous phase prepared in step a) under high shear homogenization to provide a mixture;
   d) drying the mixture prepared in c) to provide a stable powder; and
   e) agglomerating the stable powder prepared in d) by a low shear granulation process.

3. A stable herbicide powder containing built-in adjuvant which comprises:
   a) a herbicide active ingredient selected from the class of ACCase or ALS enzyme inhibitors comprising, with respect to the total composition, from about 1 gram per kilogram (g/kg) to about 200 g/kg;
   b) a built-in adjuvant comprising, with respect to the total composition, from about 50 g/kg to about 750 g/kg, wherein the built-in adjuvant is one or more of a nonionic surfactant or a water immiscible liquid;
   c) a solid carbohydrate comprising, with respect to the total composition, from about 10 g/kg to about 700 g/kg, wherein the solid carbohydrate is a monosaccharide, a disaccharide, or a polysaccharide, or a mixture thereof; and
   d) a solid, water soluble polymer or oligomer comprising, with respect to the total composition, from about 50 g/kg to about 700 g/kg, with the proviso that the solid carbohydrate and the solid, water soluble polymer or oligomer must together comprise at least 200 g/kg of the total composition;
   wherein the herbicide active ingredient has a water solubility of less than or about 3000 parts per million at pH of about 6.5 to about 7.5.

4. The composition of claim 1 or 3 in which the herbicide active ingredient is at least one of cyhalofop-butyl, penoxsulam, bensulfuron-methyl, azimsulfuron, imazosulfuron or fenoxaprop-P-ethyl.

5. The composition of claim 1 or 3 in which the built-in adjuvant is a water-immiscible organic liquid.

6. The composition of claim 1 or 3 in which the built-in adjuvant is one or more than one of a petroleum derived paraffinic hydrocarbon, a petroleum derived aromatic hydrocarbon, a plant derived oil or a $C_1$-$C_6$ ester of a plant derived oil.

7. The composition of claim 1 or 3 in which the solid carbohydrate is a monosaccharide or a disaccharide.

8. The composition of claim 1 or 3 in which the solid carbohydrate is sucrose.

9. The composition of claim 1 or claim 3 in which the solid, water soluble polymer or oligomer is one or more than one of a lignosulfonate, a polyvinyl alcohol or an alkyl naphthalene sulfonate formaldehyde condensate.

10. The composition of claim 1 or 3 in which the herbicide active ingredient is cyhalofop-butyl, fenoxaprop-ethyl, fluazifop-P-butyl, haloxyfop-methyl, haloxyfop-R-methyl, metamifop, propaquizafop, quizalofop-P-ethyl, quizalofop-P-tefuryl, profoxydim, azimsulfuron, bensulfuron-methyl, cloransulam-methyl, cyclosulfamuron, diclosulam, ethoxysulfuron, florasulam, flucetosulfuron, flumetsulam, halosulfuron-methyl, metazosulfuron, metosulam, metsulfuron, penoxsulam, primisulfuron-methyl, propyrisulfuron, pyrazosulfuron-ethyl, pyroxsulam, imazethapyr, imazamox, or imazosulfuron, or a derivative thereof.

11. The composition of claim 1 or 3 in which the herbicide active ingredient is cyhalofop-butyl.

12. The composition of claim 1 or 3 in which the herbicide active ingredient is clethodim, clodinafop-propargyl, cycloxydim, sethoxydim, tralkoxydim, bispyribac-sodium, cinosulfuron, pyribenzoxim, pyriftalid, pyriminobac-methyl, pyrimisulfan, imazapyr, or triafamone, or a derivative thereof.

13. The composition of claim 1 or 3 in which the herbicide active ingredient is cyhalofop-butyl, fenoxaprop-ethyl, fluazifop-P-butyl, haloxyfop-methyl, haloxyfop-R-methyl, metamifop, propaquizafop, quizalofop-P-ethyl, quizalofop-P-tefuryl, penoxsulam, clodinafop-propargyl, pyribenzoxim, pyriftalid, pyriminobac-methyl, or triafamone.

14. The composition of claim 1 or 3 in which the herbicide active ingredient is cloransulam-methyl, diclosulam, metosulam, or pyroxsulam.

15. The composition of claim 4 in which the built-in adjuvant is present in an amount of about 200 g/kg to about 600 g/kg relative to the total composition.

16. The composition of claim 4 in which the built-in adjuvant is present in an amount of about 300 g/kg to about 600 g/kg relative to the total composition.

17. The composition of claim 11 in which the built-in adjuvant is present in an amount of about 200 g/kg to about 600 g/kg relative to the total composition.

18. The composition of claim 11 in which the built-in adjuvant is present in an amount of about 300 g/kg to about 600 g/kg relative to the total composition.

19. A stable herbicidal solid composition containing built-in adjuvant which comprises:

a) an herbicide selected from the compounds of the Formula

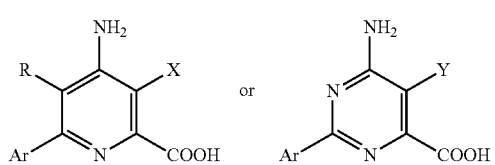

wherein
Ar represents a phenyl group substituted with one to four substituents independently selected from the group consisting of halogen, $C_1$-$C_6$ alkyl, $C_1$-$C_6$ alkoxy, $C_2$-$C_4$ alkoxyalkyl, $C_2$-$C_6$ alkylcarbonyl, $C_1$-$C_6$ alkylthio, $C_1$-$C_6$ haloalkyl, $C_1$-$C_6$ haloalkoxy, $C_2$-$C_4$ haloalkoxyalkyl, $C_2$-$C_6$ haloalkylcarbonyl, $C_1$-$C_6$ haloalkylthio, —OCH$_2$CH$_2$—, —OCH$_2$CH$_2$CH$_2$—, —OCH$_2$O—, and —OCH$_2$CH$_2$O—;
R represents H or F;
X represents Cl or vinyl;
Y represents Cl, vinyl or methoxy; and
their salts and esters;

comprising, with respect to the total composition, from about 1 gram per kilogram (g/kg) to about 200 g/kg;

b) a built-in adjuvant comprising, with respect to the total composition, from about 50 g/kg to about 750 g/kg, wherein the built-in adjuvant is one or more of a nonionic surfactant or a water immiscible liquid;

c) a solid carbohydrate comprising, with respect to the total composition, from about 10 g/kg to about 700 g/kg, wherein the solid carbohydrate is a monosaccharide, a disaccharide, or a polysaccharide, or a mixture thereof; and d) a solid, water soluble polymer or oligomer comprising, with respect to the total composition, from about 50 g/kg to about 700 g/kg, with the proviso that the solid carbohydrate and the solid, water soluble polymer or oligomer must together comprise at least 200 g/kg of the total composition, wherein the herbicide active ingredient has a water solubility of less than or about 3000 parts per million at pH of about 6.5 to about 7.5.

20. The composition of claim 19 wherein the herbicide is a compound of the following structure

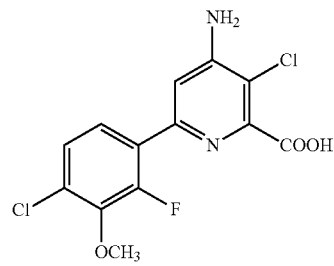

wherein R equals H or a $C_1$-$C_6$ alkyl group.

21. A method of controlling undesirable vegetation in an aquatic environment which comprises broadcasting, spraying or adding an herbicidally effective amount of the composition of any one of claim 1, 3, 19 or 20 to an aquatic environment either before emergence or after emergence of the undesirable vegetation.

22. A method of controlling undesirable vegetation in a flooded rice paddy which comprises broadcasting, spraying or adding an herbicidally effective amount of the composition of any one of claim 1, 3, 19 or 20 to an aquatic environment either before emergence or after emergence of the undesirable vegetation.

23. A method of preparing the stable herbicidal granule composition of any one of claim 19 or 20, wherein the composition is a granule, which comprises:

a) mixing all solid, water soluble polymers or oligomers and solid carbohydrate ingredients in water to form an aqueous phase;

b) mixing the built-in adjuvant and oil soluble or oil dispersible active ingredients to form an oil phase;

c) adding the oil phase prepared in step b) to the aqueous phase prepared in step a) under high shear homogenization to provide a mixture;

d) drying the mixture prepared in c) to provide a stable powder; and e) agglomerating the stable powder prepared in d) by a low shear granulation process.

24. The composition of claim 19 in which the herbicide active ingredient comprises a compound of the Formula

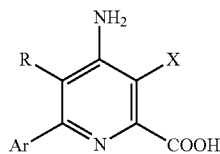

wherein Ar represents a phenyl group substituted with one to four substituents independently selected from the group consisting of halogen and $C_1$-$C_6$ alkoxy; R represents H or F; and X represents Cl or vinyl; or a salt or ester thereof.

25. The composition of claim 24 in which the herbicide active ingredient comprises a compound of the Formula

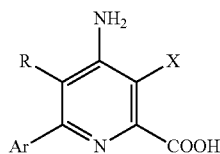

wherein
Ar represents

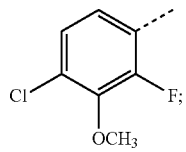

R represents F; and
X represents Cl;
or a salt or ester thereof.

26. The composition of claim 20, wherein R is methyl.

27. The composition of any one of claim 1, 3 or 19 in which the built-in adjuvant is a liquid or a solid.

28. The composition of any one of claim 1, 3 or 19 in which the built-in adjuvant is one or more of a non-ionic surfactant, which is a polyol fatty acid ester, polyethoxylated ester, polyethoxylated alcohol, alkyl polysaccharide or blends thereof, alkyl polyglycoside or blends thereof, amine ethoxylate, sorbitan fatty acid ester ethoxylate, organosilicone based surfactant, ethylene vinyl acetate terpolymer, ethoxylated alkyl aryl phosphate ester, or sucrose ester of fatty acid.

29. The composition of any one of claim 1, 3 or 19 in which the built-in adjuvant is one or more of a water immiscible liquid, which is a petroleum fraction, hydrocarbon, mineral oil, kerosene, paraffinic oil, mixed naphthalene and alkyl naphthalene fraction, aromatic solvent, alkyl substituted benzene, xylene, propylbenzene fraction, plant derived oil, soybean oil, rape seed oil, olive oil, castor oil, sunflower seed oil, coconut oil, corn oil, cotton seed oil, linseed oil, palm oil, peanut oil, safflower oil, sesame oil, tung oil, ester of plant derived oil, 2-ethyl hexyl stearate, n-butyl oleate, isopropyl myristate, propylene glycol dioleate, methyl soyate, ester of diacid, di-octyl succinate, di-butyl adipate, di-octyl phthalate, or ditridecyl phthalate.

30. The composition of any one of claim 1, 3 or 19 in which the built-in adjuvant is one or more of a plant derived oil, independently selected from the group consisting of soybean oil, rape seed oil, olive oil, castor oil, sunflower seed oil, coconut oil, corn oil, cotton seed oil, linseed oil, palm oil, peanut oil, safflower oil, sesame oil, and tung oil, a $C_1$-$C_6$ ester of plant derived oil, a methylated seed oil, or a methyl soyate.

31. The composition of any one of claim 1, 3 or 19 in which the built-in adjuvant is present in an amount of about 200 g/kg to about 600 g/kg relative to the total composition.

32. The composition of any one of claim 1, 3 or 19 in which the built-in adjuvant is present in an amount of about 300 g/kg to about 600 g/kg relative to the total composition.

33. The composition of any one of claim 1, 3 or 19 further comprising one or more of a pesticide active ingredient, a plant growth regulator, or a safener.

34. The composition of claim 33, wherein the one or more of a pesticide active ingredient is selected from: clodinafop-propargyl, clethodim, cycloxydim, diclofop-methyl, fenoxaprop-ethyl+isoxidifen-ethyl, pinoxaden, sethoxydim, tepraloxydim, tralkoxydim, 2,4-D esters and amines, 2,4-MCPA, 2,4-MCPA esters and amines, acetochlor, acifluorfen, alachlor, amidosulfuron, aminopyralid, aminotriazole, ammonium thiocyanate, anilifos, benfuresate, bentazon, bentazone-sodium, benthiocarb, benzobicyclon, benzofenap, bifenox, bispyribac-sodium, bromobutide, butachlor, cafenstrole, carfentrazone-ethyl, chlorimuron, chlorpropham, cinosulfuron, clomazone, clomeprop, clopyralid, cumyluron, daimuron, diflufenican, dimepiperate, dimethametryn, diquat, dithiopyr, EK2612, EPTC, esprocarb, ET-751, ethbenzanid, fenoxasulfone, fentrazamide, flazasulfuron, fluazifop, flufenacet, flufenpyr-ethyl, flumioxazin, flupyrsulfuron, fluroxypyr, fluroxypyr esters and salts, fomesafen, foramsulfuron, glufosinate, glufosinate-P, glyphosate, imazamethabenz, imazapic, imazapyr, imazaquin, indanofan, ioxynil, ipfencarbazone, isoxaben, MCPB, mefenacet, mesosulfuron, mesotrione, metolachlor, molinate, monosulfuron, MSMA, orthosulfamuron, oryzalin, oxadiargyl, oxadiazon, oxazichlomefone, oxyfluorfen, paraquat, pendimethalin, pentoxazone, pethoxamid, picloram, piperophos, pretilachlor, prohexadione-calcium, propachlor, propanil, propisochlor, propyzamide, prosulfuron, pyrabuticarb, pyraclonil, pyrazogyl, pyrazolynate, pyrazoxyfen, pyribenzoxim, pyridate, pyriftalid, pyriminobac-methyl, pyrimisulfan, quinoclamine, quinclorac, S-3252, simazine, simetryne, s-metolachlor, sulcotrione, sulfentrazone, sulfosate, tefuryltrione, thenylchlor, thiazopyr, thiobencarb, triafamone, triclopyr, triclopyr-esters and amines, trifluralin, trinexapac-ethyl, and tritosulfuron.

35. The composition of claim 33, wherein the one or more of a safener is selected from benoxacor, benthiocarb, cloquintocet-mexyl, daimuron, dichlormid, dicyclonon, dimepiperate, fenchlorazole-ethyl, fenclorim, flurazole, fluxofenim, furilazole, Harpin proteins, isoxadifen-ethyl, mefenpyr-diethyl, mephenate, MG 191, MON 4660, naphthalic anhydride (NA), oxabetrinil, R29148, and N-phenyl-sulfonylbenzoic acid amides, and derivatives thereof.

36. The composition of claim 33, wherein the one or more of a safener is cloquintocet-mexyl.

37. The composition of any one of claim 1, 3 or 19 in which the solid carbohydrate is one or more than one of dextrine, starch, modified starch, modified cellulose, or natural gum, or mixtures thereof.

38. The composition of any one of claim 1, 3 or 19 in which the solid carbohydrate is one or more than one of mono- or disaccharide, selected from glucose, fructose, sucrose, trehalose, lactose and maltose.

39. The composition of any one of claim 1, 3 or 19 in which the solid, water soluble polymer or oligomer is one or more than one of lignosulfonate, alkyl naphthalene sulfonate formaldehyde condensate, polyvinyl alcohol, polyacrylate, polyethylene oxide, or polyvinylpyrrolidone, or co-polymers, derivatives, or mixtures thereof.

40. The composition of any one of claim 1, 3 or 19 in which the solid, water soluble polymer or oligomer is one or more than one of lignosulfonate; polyvinyl alcohol derived from the hydrolysis of polyvinyl acetate, that vary in the degree of hydrolysis from about 87 to about 99%; or alkyl naphthalene sulfonate formaldehyde condensate; or co-polymers, derivatives or mixtures thereof.

41. The composition of any one of claim 25 or 26 in which the built-in adjuvant is present in an amount of about 200 g/kg to about 600 g/kg relative to the total composition.

42. The composition of any one of claim 25 or 26 in which the built-in adjuvant is present in an amount of about 300 g/kg to about 600 g/kg relative to the total composition.

43. The composition of claim 19, which is a granule.

44. The composition of claim 19, which is a powder.

45. The composition of claim 19, in which the built-in adjuvant is a water-immiscible organic liquid.

46. The composition of claim 19, in which the built-in adjuvant is one or more than one of a petroleum derived paraffinic hydrocarbon, a petroleum derived aromatic hydrocarbon, a plant derived oil or a $C_1$-$C_6$ ester of a plant derived oil.

47. The composition of claim 19, in which the solid carbohydrate is a monosaccharide or a disaccharide.

48. The composition of claim 19, in which the solid carbohydrate is sucrose.

49. The composition of claim 19, in which the solid, water soluble polymer or oligomer is one or more than one of a lignosulfonate, a polyvinyl alcohol or an alkyl naphthalene sulfonate formaldehyde condensate.

* * * * *